United States Patent
Lammers et al.

(10) Patent No.: US 11,925,198 B2
(45) Date of Patent: Mar. 12, 2024

(54) PROCESS FOR ENCAPSULATING NATURAL FOLLISTATIN

(71) Applicant: Deutsches Institut für Lebensmitteltechnik e.V., Quakenbrück (DE)

(72) Inventors: Volker Lammers, Quakenbrück (DE); Volker Heinz, Quakenbrück (DE); Aleksandar Pajic, Quakenbrück (DE); Matthias Rumker von Hoven, Quakenbrück (DE); Carolin Bommes, Quakenbrück (DE)

(73) Assignee: Deutsches Institut für Lebensmitteltechnik e.V., Quakenbrück (DE)

( * ) Notice: Subject to any disclaimer, the term of this patent is extended or adjusted under 35 U.S.C. 154(b) by 0 days.

(21) Appl. No.: 17/503,845

(22) Filed: Oct. 18, 2021

(65) Prior Publication Data

US 2022/0117289 A1    Apr. 21, 2022

(30) Foreign Application Priority Data

Oct. 16, 2020  (DE) .......................... 102020213091.4

(51) Int. Cl.
- A23P 10/35 (2016.01)
- A23J 1/02 (2006.01)
- A23J 1/08 (2006.01)
- A23L 33/17 (2016.01)

(52) U.S. Cl.
CPC .................. *A23P 10/35* (2016.08); *A23J 1/02* (2013.01); *A23J 1/08* (2013.01); *A23L 33/17* (2016.08)

(58) Field of Classification Search
CPC ... A23P 10/35; A23L 33/17; A23J 1/02; A23J 1/08

USPC ......................................................... 426/656
See application file for complete search history.

(56) References Cited

U.S. PATENT DOCUMENTS

| | | | |
|---|---|---|---|
| 2007/0275036 A1* | 11/2007 | Green, III | A61K 38/1709 514/10.2 |
| 2011/0236557 A1 | 9/2011 | Suzuki et al. | |

FOREIGN PATENT DOCUMENTS

| | | |
|---|---|---|
| DE | 102009014137 A1 | 9/2010 |
| EP | 0824000 A1 | 2/1998 |
| EP | 2883461 A1 | 6/2015 |
| EP | 2806745 B1 | 10/2015 |
| EP | 2883461 B1 | 11/2017 |
| JP | 2003009837 A | 2/2007 |

(Continued)

OTHER PUBLICATIONS

Translation of KR-20080036311-A (Year: 2008).*
European Search Report from the corresponding European Patent Application No. EP 21 20 3282, dated Mar. 4, 2022.

*Primary Examiner* — Brent T O'Hern
(74) *Attorney, Agent, or Firm* — Greer, Burns & Crain, Ltd.; Steven P. Fallon

(57) ABSTRACT

A process for the production of fat-encapsulated follistatin. The process includes steps of a) metering fat having a melting point of at least 40° C. into an extruder, b) heating the fat in the extruder during rotation of the at least one screw, c) metering the follistatin into the extruder barrel to produce a flowable mixture, d) cooling the flowable mixture in a downstream adjacent section of the extruder barrel, e) subsequently discharging the mixture through an extruder die, and f) comminuting the mixture after it discharges from the extruder die.

16 Claims, 2 Drawing Sheets

(56) References Cited

FOREIGN PATENT DOCUMENTS

KR  20080036311 A  *  4/2008
WO   2013101591 A2    7/2013

* cited by examiner

PROCESS FOR ENCAPSULATING NATURAL FOLLISTATIN

PRIORITY CLAIM

This application claims priority under 35 U.S.C. § 119 and all applicable statutes and treaties from prior German patent application 10 2020 213 091.4, filed on 16 Oct. 2020.

FIELD OF THE INVENTION

The present invention relates to a process for encapsulating natural follistatin, in particular for use in foodstuffs and feedstuffs.

BACKGROUND

EP2806745 B1 for the production of biologically active follistatin describes the treatment of raw liquid egg yolk, of whole egg or of egg white from fertilized bird eggs or of raw animal blood serum with high pressure of at least 4500 bar or with pulsed electric fields of at least 5 kV/cm at a flow rate of 30 L/h. EP 2 883 461 B1 for the production of biologically active follistatin describes that from egg yolk, whole egg or egg white from fertilized bird eggs or from raw animal blood serum, first a fraction containing follistatin is precipitated, which is subsequently treated by high pressure or pulsed electric fields.

Brodkorb et al, Nature Protocols 2019 (https://doi.org/10.1038/s41596-018-0119-1) describe an in vitro test for the simulation of digestion.

SUMMARY OF THE INVENTION

The invention provides an alternative process for producing a formulation of natural follistatin which is shelf-stable at room temperature, and alternative shelf-stable and preserved follistatin, preferably a formulation of natural follistatin, that is resistant to gastric juice and provides biologically available follistatin. The preferred process is simple to carry out and produces shelf-stable follistatin, preferably without a step of drying the raw material containing follistatin. Further preferably, the preserved follistatin can be free-flowing at room temperature, can be easy to dose, and/or after consumption, the formulation can release follistatin only after entry into the small intestine.

BRIEF DESCRIPTION OF THE DRAWINGS

The invention will now be described in more detail with reference to an example and with reference to the figures.

DETAILED DESCRIPTION OF THE PREFERRED EMBODIMENTS

Figure 1:
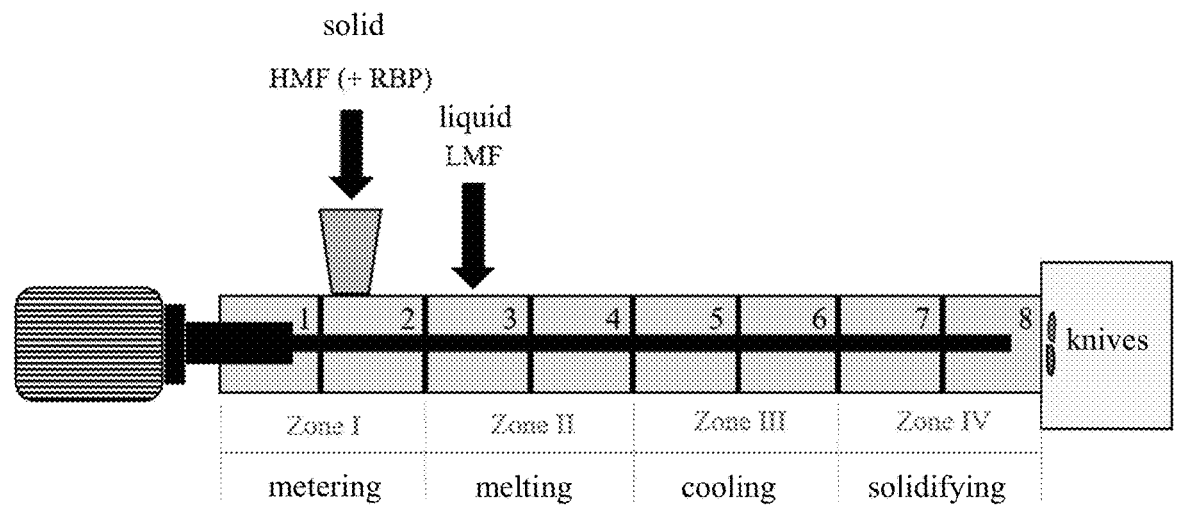
FIG. 1 schematically shows an extruder preferably used for process of the invention for encapsulating natural follistatin.

The present invention relates to a process for encapsulating natural follistatin, in particular for use in foodstuffs and feedstuffs. The natural follistatin can be present in dry form, in solid or in liquid composition. In particular at 20° C. to 40° C. or up to 38° C., the encapsulated follistatin is solid or liquid, and the encapsulated follistatin obtainable by the process is usable as an additive for foodstuff and feedstuff. The follistatin can be present in the form of fertilized bird eggs, in particular fertilized chicken eggs, in the form of whole egg, egg yolk or egg white from fertilized bird eggs and/or in the form of raw animal blood serum, optionally including the step of concentrating a follistatin containing fraction from the whole egg, egg yolk or egg white and/or animal blood serum by precipitating a soluble protein fraction containing follistatin and separating the precipitated fraction prior to preservation of the follistatin and prior to encapsulation. The preservation, which is a sterilization of the follistatin-containing whole egg, egg yolk or egg white from fertilized bird eggs and/or of the follistatin-containing raw animal blood serum, is e.g. carried out by gamma irradiation, preferably by high pressure treatment and/or by treatment with pulsed electric fields.

The process is characterized in that in relation to the encapsulation material, a very high volume portion of follistatin, in dry or liquid form, is encapsulated, and in that the process can be carried out with little machine effort. The obtainable encapsulated follistatin is preferably characterized in that it has a low content of encapsulation material. In particular, the encapsulated follistatin is characterized in that it is stable at room temperature and without an additive is free-flowing and easy to dose. Optionally, the encapsulated follistatin is resistant to gastric juice, so that the follistatin is released from the encapsulation only after entry into the small intestine or during passage of the small intestine.

Further, the invention relates to the use of the encapsulated follistatin to improve muscle gain and/or muscle regeneration, in particular by administering the encapsulated follistatin as an additive to food.

The invention achieves the object by the features of the claims and in particular provides a process for the production of fat-encapsulated follistatin, the process including the steps of a) metering fat, which optionally is a fat mixture, having a melting point of at least 40° C., preferably of at least 50° C., more preferably at least 55° C., e.g. 50 to 90° C., preferably 55 to 70° C., more preferably at least 60 to 70° C., into an extruder, b) during rotation of the at least one screw of the extruder, heating the fat, e.g. to a temperature at which the fat is flowable, which temperature is e.g. 35 to 40 K above the melting temperature of the fat, e.g. at maximum 30 K or at maximum 25 K or at maximum 20 K or at maximum 10 K above the melting temperature of the fat, optionally to at maximum the melting temperature of the fat, to produce flowable fat, c) metering the follistatin into the extruder barrel, preferably downstream of the fat metering or at the same location as the fat metering, and mixing the follistatin with the fat in the extruder barrel to produce a flowable mixture containing or consisting of the fat and the follistatin, d) in the extruder, cooling the flowable mixture to the melting temperature of the fat or below, such that e.g. a viscous but still flowable consistency is obtained, preferably by cooling the mixture to a temperature that is in a range of at least 1 K, at least 2 K, at least 3 K, at least 4 K or at least 5 K, preferably at least 10 K, more preferably at least 15 K, more preferably at least 20 K or at least 25 K or at least 30 K, e.g. at least 35 to 50 K or up to 40 K below the melting temperature of the fat or mixture, e) immediately subsequently pressing or resp. extruding the mixture through an extruder die which e.g. has die openings having a diameter of 250 µm to 6 mm, more preferably 500 µm to 3 mm or up to 2 mm or up to 1 mm, to produce at least one extrudate strand, and,
f) after discharge from the extruder die, comminuting the extrudate strand, e.g. by cutting, to produce pellets from the mixture,
g) optionally subsequent drying of the pellets, e.g. until the surface is dry, preferably at a temperature below the melting temperature of the fat,
h) optionally and preferably subsequent treatment of the pellets by temperature-controlling to a temperature of at least 2 to 10 K below the melting temperature of the fat and at least 50° C., preferably at least 55° C., more preferably at least 58° C., still more preferably at least 60° C., for at least 1 d, more preferably 3 to 10 d, e.g. 5 to 7 d, or consisting thereof.

Generally, in the process, at least during steps a), b), c), d) and e), the at least one screw of the extruder is rotated without interruption.

Optionally, after heating the fat, which is metered in step a) and e.g. has a melting point of at least 50° C., to at least its melting temperature in step b), and prior to cooling the flowable mixture in the extruder in step d), a low-melting fat is metered into the extruder. The low-melting fat is preferably metered in to at maximum 20 wt.-%, more preferably to at maximum 19 wt.-%, to at maximum 18 wt.-%, to at maximum 17 wt.-%, even more preferably to at maximum 16 wt.-% of the sum of the fats. Therein, the low-melting fat is e.g. added to at least 5 wt.-% or at least 10 wt.-% or at least 12 wt.-% of the sum of the fats. The sum of the fats is the mass of the fat metered in step a), e.g. having a melting point of at least 50° C., and the low-melting fat. The low-melting fat has a melting point of at maximum 40° C., preferably of at maximum 39° C., of at maximum 38° C. or of at maximum 37° C., at maximum 36° C. or at maximum 35° C. Optionally, the low melting fat can be one that is liquid at room temperature, such as nonhydrogenated plant-based oil.

The fat which is metered in step a) is preferably metered into the extruder as a solid, e.g. as powder or granules. The low-melting fat is preferably metered into the extruder as a liquid.

Currently, it is assumed that the follistatin is released from the encapsulated follistatin in the small intestine by lipases only after passing through the stomach, because the melting temperature of the fat used as encapsulant is higher than the body temperature of humans, farm animals and domestic animals. This is advantageous for follistatin because it can be attacked in the stomach by acid and digestive enzymes and should be released only after passing through the stomach, e.g. in the small intestine. Preferably, the encapsulated follistatin finds use as foodstuff or drug for humans or monogastric animals, in particular monogastric farm animals or domestic animals, e.g. for the treatment of or prevention of muscle wasting.

When metering a low-melting fat into the extruder, pellets could be produced that contain the low-melting fat and yet release the ingredient only after a time and temperature equivalent to passage into the small intestine. It is believed that the low-melting fat accelerates the dissolution of the fat metered in step a), and which e.g. has a melting point of at least 50° C.

It has shown that when a low-melting fat is metered in after step b) and prior to step d), a particulate mixture that is solid at room temperature is produced despite the content of low-melting fat. This particulate mixture, also referred to as pellets, is decomposed in the intestinal tract, particularly in the small intestine, of mammals and humans and releases the ingredient. It has shown that by choosing the type and proportion of low-melting fat, the release of the ingredient can be predetermined.

The raw material containing follistatin, also referred to herein simply as follistatin, is preferably whole egg, egg yolk or egg white from fertilized bird eggs, in particular from fertilized chicken eggs, and/or is raw animal blood serum, optionally treated by the step of concentrating a follistatin containing fraction from the whole egg, egg yolk or egg white and/or animal blood serum by precipitating a soluble protein fraction containing follistatin and separating the precipitated fraction prior to preserving the follistatin.

The step of concentrating is preferably carried out by precipitation by acidification, e.g. to pH 6 to pH 5, and/or by addition of water-soluble salt, e.g. ammonium acetate, NaCl, $NaHCO_3$, KCl and/or ammonium sulfate, and/or by addition of a solvent, e.g. ethanol. The acidification, especially in the case of egg white, can occur by fermentation of the starting material, while the concentration of sugar is reduced by addition of acid-producing bacteria or yeasts. The acidification can occur by adding acid, e.g. citric acid, lactic acid, phosphoric acid, or hydrochloric acid. The separation of a precipitated protein fraction containing follistatin can e.g. occur from egg white under natural gravity, preferably by centrifugation at at least 800×g, preferably at least 1000×g.

The preserving and/or sterilizing of the follistatin, in particular of the whole egg, egg yolk or egg white from fertilized bird eggs and/or of the raw animal blood serum, optionally treated by the step of concentration, is preferably carried out at a temperature of below 38° C., preferably below 20° C., more preferably below 10° C., by treating with a pressure of at least 4000 bar for at least 1 min, preferably up to 5500-6500 bar, more preferably up to 6000 bar for at least 1 min, preferably for 3 min, more preferably for at least 5 min, preferably using an adiabatic compression and pressure release, and/or by treatment with a pulsed electric field, in particular in a continuous process, while the follistatin, in particular egg yolk, egg white or whole egg and/or raw animal blood serum, are pumped through a space limited by at least two discharge electrodes, which e.g. generate an electric field strength of 5 to 40 kV/cm, e.g. at 12 kV/cm, at a flow rate of 30 L/h at a temperature of 30° C., preferably using unipolar pulses having a pulse duration of 5 to 20 µs, preferably of 10 µs, at a repetition rate of 70 to 200 Hz, in particular of positive square pulses. At an energy input of 50 to 140 kJ/kg, the reduction of bacterial load, determined as CFU, by a factor of 10 or 630 was obtained for egg yolks. Preferably, the bird eggs are obtained from chickens, i.e. *Gallus domesticus*.

These steps for the preservation or resp. sterilization of follistatin, which in particular is contained in egg yolk, egg white or whole egg and/or in raw animal blood serum, are non-thermal process steps, i.e. an increase in the temperature that can occur during the high pressure treatment and/or during the treatment in the pulsed electric field is not causative for the reduction of micro-organisms, in particular of bacteria, to achieve the preservation and sterilization. Additionally, the embodiments of the preservation steps are physical treatment processes, i.e. without the addition of antimicrobial chemical compounds. Accordingly, the embodiments of the preservation step are non-thermal process steps consisting of physical treatment steps that do not generate radicals and therefore maintain the chemical structure of the ingredients, in particular of unsaturated fatty acids and vitamins of the composition.

It has been found that the high pressure treatment and/or treatment in the pulsed electric field of the follistatin-containing material, which is preferably liquid whole egg, liquid egg white, preferably liquid egg yolk and/or animal blood serum, effectively reduces the bacterial contamination by a factor of at least 10, preferably by a factor of at least 100, more preferably of at least 1000. For example, for high pressure treatment, a reduction of the bacterial contamination to about 50 CFU/g, corresponding to a reduction by a factor of 3000 was found when starting from raw liquid egg yolk having a natural bacterial content of $1.5 \times 10^5$ CFU/g. For treatment in the pulsed electric field, a reduction by a factor of 10 to a factor of 1000 was found. The reduction of the natural microbiological contamination by the high pressure treatment and/or the treatment in the pulsed electric field is sufficient for preserving the egg white, whole egg or egg yolk. This reduction in microbiological load is also referred to herein as preservation and/or sterilization.

Optionally, following the preservation step, the process includes drying, in particular freeze-drying the liquid egg preparation, in particular egg yolk, egg white or whole egg or animal blood serum, resulting in an egg-containing powder, in particular in a powder containing egg yolk, egg white or whole egg or animal blood serum powder, in particular in a powder essentially consisting of the high pressure treated and/or pulsed electric field treated egg or egg components, e.g. components of egg yolk, egg white, whole egg or blood serum. In an alternative to freeze drying, the drying can be fluidized bed drying, preferably at a temperature at or below 42° C., more preferably at or below 40° C., more preferably at or below 38° C. or at or below 35° C.

According to the invention, the material containing follistatin is preferably mixed in liquid form, i.e. without drying, with fat in the extruder and this mixture is extruded. This is because it has shown that also liquid egg yolk, egg white, whole egg, or animal blood serum, optionally after a step of concentration, can be extruded by the process after the preservation and/or sterilization by high pressure treatment and/or treatment in a pulsed electric field to form a storage-stable mixture with fat containing biologically active follistatin.

It has been found that the process for producing the follistatin-containing composition including a preservation step including or consisting of high pressure treatment and/or treatment in the pulsed electric field, optionally followed by drying, preferably without drying of the follistatin, results in both an effective reduction in the bacterial contamination, e.g. determined as living bacteria, and in the follistatin retaining its biological activity, e.g. to at least 50%, preferably to at least 70%, more preferably to at least 80%, more preferably to at least 85%, to at least 90%, or to at least 95%, with respect to the biological follistatin activity in the starting material used. The mixture produced by the process including or consisting of the fat and the follistatin-containing material, or resp. follistatin, is also referred to as fat-encapsulated follistatin and can also be referred to as fat capsule.

Particularly with respect to preservation methods using irradiation, it is an advantage of the process of the invention that no radicals are generated by the preservation step and therefore the obtained preserved liquid egg yolk, egg white or whole egg or animal blood serum, which is preferably not subsequently dried, contains fewer or no radicals and reaction products of radicals. For example, the preserved liquid egg yolk, egg white or whole egg as well as the dried, preferably freeze-dried preserved egg yolk, egg white or whole egg contains the unsaturated fatty acids of the egg yolk substantially in their natural state and constitution, e.g. without changes in their double bonds. Accordingly, the composition obtainable by the process of the invention preferably contains the unsaturated fatty acids of the egg yolk without changes in their double bonds, i.e. in their natural biological state.

Preferably, in the process, no chemical preservative is added, e.g. no anti-microbial agent is added. Optionally, an antioxidant is added, e.g. ascorbic acid or a neutral salt thereof. Preferably, the whole egg, egg white, more preferably egg yolk only is free from added ingredients, e.g. the whole egg, egg white, or more preferably the egg yolk, or the animal blood serum, optionally after concentration, is subjected to the physical process steps only, which include, preferably consist of subjecting liquid whole egg, egg white or liquid egg yolk or animal blood serum to high pressure treatment and/or to treatment in the pulsed electric field, optionally followed by drying, e.g. freeze-drying or fluidized bed drying, or preferably in liquid form.

For high pressure treatment, it is preferred that the liquid whole egg, white of egg or liquid egg yolk or animal blood serum is contained in sealed containers having an elastic wall, e.g. in plastic bags, more preferably free from gas, more preferably degassed. For a gas-free whole egg, egg white or liquid egg yolk or animal blood serum in a container, gas bubbles can be expelled before sealing the container. For degassing, a reduced pressure can be applied prior to high pressure treatment, preferably also prior to treatment in the pulsed electric field.

The high pressure treatment is generally carried out using water as a compression medium that is pumped into a sealed chamber containing the liquid whole egg, egg white or liquid egg yolk or animal blood serum until the high pressure is reached, maintaining the high pressure, and then releasing the pressure, e.g. by opening the high pressure container.

It was found that after high pressure treatment within sealed containers, e.g. in sealed polyethylene bags, the preparation of liquid whole egg, egg white or liquid egg yolk preparation is stable, e.g. for 12 to 24 hours, preferably for 2 to 5 days, e.g. at 5 to 10° C., without a drastic increase in bacterial contamination, and especially without a significant loss of follistatin activity. For high pressure treatment, the adiabatic increase in temperature due to the high pressure preferably is counteracted by cooling the liquid whole egg, egg white or liquid egg yolk to a temperature which is at least 5° C., preferably about 10° C. below the maximum temperature, e.g. below 38° C. prior to the treatment. Preferably, prior to high pressure treatment and/or prior to the treatment in the pulsed electric field, the liquid whole egg, egg white or liquid egg yolk is cooled to a temperature of between 0 and 28° C., preferably to 5 to 20° C., more preferably to a maximum of 10° C.

For treatment in the pulsed electric field, it was found that a short rise in temperature, e.g. to a maximum of 45° C., preferably to a maximum of 42° C. or to 40° C., for maximally 10 s, preferably for maximally 5 or maximally 2 s results in a low loss of active follistatin. Accordingly, for the treatment in the pulsed electric field, the aforementioned short rise in temperature is acceptable, although less preferred.

Active follistatin was determined by size separation, e.g. by size-exclusion HPLC or by SDS-polyacrylamide gel electrophoresis (SDS-PAGE), optionally followed by Western blotting and immunospecific detection using an anti-follistatin antibody. A reduction of the size-specific signal identified in fresh yolk from fertilized eggs was used as an indicator for the reduction of follistatin activity, because an inactivation of follistatin results in the change, e.g. reduction of the molecule size.

Preferably, the process includes a step of concentrating the whole egg, egg white or egg yolk of the fertilized eggs. For concentrating, the fraction of whole egg, of egg white or of egg yolk having the higher proportion of follistatin is used, the fraction being obtained e.g. by size separation or by density separation. The preferred fraction is the fraction containing the egg yolk membrane, e.g. obtained from separating egg yolk or whole egg, and the fraction containing chalazae, e.g. obtained from separating the white of egg or whole egg. Preferably, the preferred fraction contains the major portion of the egg yolk membranes and/or of the chalazae of the whole egg, egg white or egg yolk subjected to the concentrating or separating step. For separating by size separation, sieving can be used, e.g. of a mesh size of 0.5 mm to 2 mm, preferably approx. 0.5 to 1 mm. Using size separation, the preferred fraction is the egg yolk membrane and/or chalazae containing fraction, which is the particulate or large fraction. For separating by density separation, centrifugation, e.g. using a centrifugal separator. Using density separation of whole egg, egg white or egg yolk, the higher density fraction is the preferred fraction.

Optionally, prior to the step of concentrating the whole egg, egg white or egg yolk of the fertilized eggs by separating the fraction containing the egg yolk membrane and/or chalazae, the whole egg, egg white or egg yolk can be diluted to facilitate the separating step, e.g. using water as a diluent, the water optionally containing salt.

In the alternative or in addition to whole egg, egg white or egg yolk of fertilized eggs, the process can be carried out using blood serum from slaughtered animals as the starting material. Accordingly, the blood serum can replace the whole egg, egg white or egg yolk in the process, and therefore the description relating to whole egg, egg white or egg yolk also refers to blood serum. In this embodiment, the process for producing a composition containing biologically active follistatin includes the step of providing raw animal blood serum and subjecting the raw animal blood serum to the preservation step while maintaining the temperature at or below 38° C., wherein the preservation step is the high pressure treatment of at least 4500 bar for at least 1 min, a treatment in the pulsed electric field of at least 5 kV/cm at a flow rate of 30 L/h, or a combination of the high pressure treatment and the treatment in the pulsed electric field, in order to provide a preserved liquid raw animal blood serum. The step of preservation can consist of the high pressure treatment, wherein the raw animal blood serum is filled into containers, the containers are sealed and subjected to the high pressure. The preservation step can consist of treatment in the pulsed electric field of the raw animal blood serum by an electric field of 5 to 40 kV/cm. Following the preservation step, the preserved raw animal blood serum can optionally be dried, e.g. by freeze drying or by fluid bed drying. Preferably, the preserved animal blood serum is encapsulated by fat in liquid form, in particular without a drying step. Preferably, between the high pressure treatment step and the freeze drying step, the raw animal blood serum is transported in the closed containers in which the raw animal blood serum was subjected to the high pressure treatment.

As a specific advantage of the high pressure treatment of liquid egg yolk, whole egg or egg white, it has been found that the bioavailability and digestibility of the protein, preferably of the total protein, is enhanced. Therefore, the process including the step of high pressure treatment of liquid egg yolk, whole egg or egg white is preferred for producing a preserved composition containing biologically active follistatin, in which composition the protein has increased bioavailability, e.g. increased digestibility, for example in relation to the non-treated liquid egg yolk, whole egg or egg white.

The mixing of fat having a melting point of at least 50° C. with the follistatin can optionally, e.g. for a portion or all of the fat having a melting point of at least 50° C. and for all of the follistatin, occur prior to the extrusion, e.g. in a mixer, which can be a powder mixer or an extruder, or the mixing can occur by simultaneously feeding the fat and follistatin into the extruder in which the mixture is extruded. In particular, in the embodiment in which the mixing of the fat with follistatin occurs in an extruder, the fat can have a temperature above its melting temperature or can have a temperature at or below its melting temperature. A mixer or extruder in which the fat is mixed with follistatin can be formed as an upstream section of the extruder in which the mixture is subsequently extruded. Accordingly, in the process, steps a) and c), preferably a), b) and c) can be carried out simultaneously.

The fat metering of the fat in step a), the fat preferably having a melting point of at least 50° C., is preferably carried out at the inlet end of the extruder, optionally the metering of the follistatin can be carried out in the area of the inlet end of the extruder or downstream thereof. Generally, the at least one screw of the extruder rotates continuously during the process, e.g. at the same or variable rate of rotation.

Preferably, the heating of the mixture during extrusion is carried out by temperature-controlling the extruder in a first extruder section, e.g. by heating the extruder barrel and/or the screw along a first extruder section, and by rotating the at least one screw of the extruder. Optionally, the first extruder section is not temperature-controlled, so that the heating of the mixture is predominantly or substantially exclusively carried out by mechanical energy input from the extruder screw. The cooling following the generation of a flowable mixture is preferably carried out within the same extruder in a second extruder section and within an optional third extruder section, which e.g. immediately downstream adjoin the first extruder section. For the cooling, the second extruder section and the optional third extruder section are cooled, in particular the barrel and/or the screw along the second and/or third extruder section. The second extruder section and/or the third extruder section can e.g. be cooled to 10° C. to 0° C., e.g. to a temperature of up to 70 K, of up to 50 K, of up to 40 K, of up to 35 K, of up to 30 K, of up to 25 K or up to 20 K below the melting temperature of the fat which was metered in step a), preferably below the melting temperature of the flowable mixture.

Preferably, the cooling of the second extruder section is carried out in counter-current to the conveying direction of the extruder. Optionally, the second and/or the third extruder section can be cooled in order to bring the mixture, after the discharge from the extruder die, to a temperature which is at maximum 35 K, at maximum 30 K, at maximum 25 K or at maximum 20 K below the melting temperature of the flowable mixture or below the melting temperature of the fat metered in step a). This is because it has shown that even at a temperature below the melting temperature, the mixture is forced through the die by the extruder and is solid immediately thereafter. Preferably, the comminution occurs immediately after discharge of the mixture from the die.

Generally, the melting temperature of the flowable mixture can be the melting temperature of the fat metered in step a), particularly for the purposes of temperature control in the process. The melting temperature, also referred to as the melting range, of fat, which can be a mixture, is determined by differential scanning calorimetry (DSC). Preferably, the melting temperature is the melting range determined by DSC.

The comminuting of the mixture occurs immediately after discharge of the mixture from the extruder, wherein the temperature to which the mixture has been cooled sets a viscosity that allows for the passage through a forming unit, e.g. of a die plate, preferably in combination with a cutting device. The cutting device can e.g. include rotating knives, e.g. 2 to 6 knives, running at 100 to 1500 rpm downstream adjacent to the extruder die, which e.g. is a die plate.

Since the temperature to which the mixture has been cooled when it discharges from the extruder die, is below the melting temperature of the fat or mixture by 1 to 50 K, e.g. up to 40 K or up to 30 K, e.g. by 5 to 25 K or 10 to 20 K, the mixture solidifies after passing through the forming unit already without or with little further cooling. The flowability of the mixture even at a temperature below its melting temperature, e.g. by 20 K or 10 K to 1 K below its melting temperature, is presently attributed to the fact that the mixture is pressurized and continuously sheared in the extruder. Accordingly, it is generally preferred that the mixture is continuously sheared in the extruder, e.g. by continuous rotation of the screw. The mixture discharged from the extruder solidifies immediately and, particularly after the comminution, forms pieces, which herein are also referred to as pellets and which are pourable or free-flowing at a temperature below the melting temperature of the fat and which are therefore easy to dose and to mix into foods. The pellets include or consist of the follistatin encapsulated by fat.

During the optional step h), the treatment of the pellets by temperature-controlling, this can be temperature-controlled to a temperature lying at least 2 to 10 K below the melting temperature of the fat, which has a melting point of at least 50° C. or at least 55° C., e.g. 50 to 90° C., preferably from 55 to 70° C., more preferably at least 60 to 70° C.

The process has the advantage of producing a product in the form of pellets having a high loading of follistatin-containing ingredient, represented by preserved and/or sterilized powdered or liquid egg yolk, egg white or whole egg and/or animal blood serum, a content of at least 5 wt.-%, at least 10 wt.-%, at least 20 wt.-%, at least 30 wt.-%, at least 40 wt.-% or at least 50 wt.-%, e.g. up to 60 wt.-%, balance fat.

When mixing at least a portion of the fat metered in step a) with the ingredient before they are metered into the extruder, the fat is liquid, preferably powdery, and the ingredient is powdery or liquid.

Generally, the fat and the ingredients are suitable for human or animal consumption, in particular suitable for food, and preferably of natural origin. The fat can consist of only one compound or of a mixture of at least two compounds. Preferably, the fat is of plant-based origin. The fat can be free fatty acid, optionally as salt, mono-fatty acid glyceride, di-fatty acid glyceride and/or tri-fatty acid glyceride and/or wax, or can be a mixture of at least two of these, preferably saturated. The free fatty acid, which is preferably saturated, or its salt, can have a chain length of e.g. 10 to 24 C atoms, e.g. 12 to 18 C atoms, wax can consist of at least one $C_6$ to $C_{16}$ fatty acid, esterified with at least one $C_2$- to $C_4$-alcohol.

A preferred fat that is metered in step a) includes or consists of plant-based fat and/or animal fat hardened by hydrogenation, e.g. fish oil, e.g. hardened coconut fat, hardened palm fat, hardened canola fat, hardened fish oil, or a mixture of at least two of these.

Fat that is metered in step a) preferably has a melting range of 60 to 90° C., more preferably 60 to 70° C., and is hardened by complete hydrogenation, e.g. canola oil, beet oil, sunflower oil, palm oil, palm kernel fat, palm kernel oil, castor oil, corn germ oil, peanut oil, soybean oil, wheat germ oil, olive oil, fish oil, milk fat, each completely hydrogenated, or a mixture of at least two of these.

The low melting fat is not hydrogenated and can be monounsaturated or polyunsaturated, e.g. coconut fat, palm kernel fat, palm fat, milk fat, vegetable oil, e.g. canola oil, olive oil, linseed oil, sunflower oil, hemp oil, peanut oil, walnut oil, wheat germ oil, palm oil, palm kernel oil, safflower oil, sesame oil, cottonseed oil, or a mixture of at least two of these.

The treatment of the pellets by temperature-controlling to a temperature of at least 2 to 10 K below the melting temperature of the fat metered in step a), and at least 50° C. in step h), can be carried out directly after step f), or after steps f) and g). Preferably, before step h), the pellets are filled into packages, e.g. elastic bags, e.g. of plastic. The treatment of the pellets in step h) results in a significant reduction of the microbial content, especially of bacteria. Surprisingly, it has shown that this treatment results in in the reduction of the microbial content, while the shape and the quality of the pellets remain essentially unchanged. The quality or biological activity of the ingredient contained in the pellets, in particular the biological activity of follistatin, also remained essentially unchanged by this treatment.

The extruder can have exactly one screw or can have two or more screws, e.g. can be a twin screw extruder or planetary roller extruder. Optionally, the extruder has a section arranged at the inlet end, which section is set up to comminute solids, e.g. with a smaller gap between the screw and the stator than in an adjacent first section and/or than in the second section adjacent thereto.

Optionally, the extruder has a section formed as a planetary roller extruder, e.g. as a section arranged at the inlet end, as a first section and/or as a second section. The planetary roller extruder has the advantage of very precise temperature control with low energy input, which can be advantageous for ingredients sensitive to temperature and shearing.

Example: Production of an Ingredient Encapsulated by Fat

Egg powder was used as an ingredient. For the production, fertilized hen eggs (*Gallus domesticus*) obtained from a certified breeding station were used, which eggs were not brooded. The eggs were cracked and separated into egg yolk and the white of egg automatically. As raw liquid egg yolk, 3000 L egg yolk were used that were preferably homogenized by stirring and were maintained at 5 to 10° C. and filled under sterile conditions into polyethylene bags and sealed after expulsion of entrapped air bubbles. These polyethylene bags could have a volume of between 1 L and 50 L, preferably of 5 to 20 L each. The bags were arranged in a high pressure chamber (NC-Hyperbaric, Spain). Using water as a compression medium, the pressure was increased to 6000 bar within 10 to 20 minutes. After a holding time of 3 or 5 minutes, respectively, the pressure was released by opening a release valve.

The bacterial contamination was determined by standard dilution plating on complete medium and counting following cultivation in an incubator at 37° C. for 48 h. Aliquots from the high pressure treated egg yolk were kept at about 5° C. for a few hours and subsequently freeze-dried by freezing the egg yolk and applying vacuum to withdraw water, while controlling the temperature of the egg yolk to preferably not exceed 10° C., preferably 5° C., preferably keeping the egg yolk in a frozen state.

The microbiological analysis showed that the high pressure treatment both for 3 minutes and 5 minutes resulted in a drastic reduction of bacterial contamination, and also the subsequent step of freeze-drying further reduced the bacterial contamination.

TABLE 1

Bacterial contamination, measured as CFU/g

| Sample | Salmonella in 25 g sample | total cell count (CFU/g) |
| --- | --- | --- |
| raw liquid egg yolk | negative | 1.5 × 10$^5$ |
| liquid egg yolk after 6000 bar, 3 min | negative | 50 |
| liquid egg yolk after 6000 bar, 5 min | negative | 50 |
| freeze-dried egg yolk after 6000 bar, 3 min | negative | 40 |
| freeze-dried egg yolk after 6000 bar, 5 min | negative | <10 |

CFU = colony forming units (viable micro-organisms)

CFU=colony forming units (viable micro-organisms)

Follistatin activity in the liquid egg yolk as determined by SDS-PAGE showed a reduction by approx. 15%, or a content of 85% active follistatin, on the basis of the content of active follistatin as determined by SDS-PAGE in the raw liquid yolk.

In the freeze-dried egg yolk, the content of active follistatin in relation to the total protein concentration was the same as in the liquid egg yolk after high pressure treatment. This shows that the step of freeze-drying does not substantially affect the activity of follistatin, e.g. freeze-drying does not substantially reduce the concentration of active follistatin per total protein content.

As an alternative, an aliquot of the raw liquid egg yolk used in Example 1 was treated at a flow rate of 30 L/h at 30° C. by pulsed electric field of a field strength of 12 kV/cm using unipolar positive pulses having a pulse duration of 10 µs at a repetition rate of 200 Hz. At an energy input of 50 to 140 kJ/kg, the viable bacterial contamination was reduced by a factor of 10 and 630 CFU, respectively, as determined by dilution plating.

Using SDS-PAGE, a reduction of active follistatin by approx. 15%, or a residual activity of follistatin of 85% based on the raw egg yolk was found. In the SDS-PAGE no thermal denaturation of the liquid egg yolk was observed.

Optionally, for concentrating prior to high pressure treatment or resp. treatment in the pulsed electric field, the egg yolk was separated by centrifugation at 3343×g for 20 min into a high density fraction that was collected as a pellet and a low density supernatant fraction. The high follistatin fraction was found to be the high density fraction.

In the alternative, whole egg or egg white was separated by centrifugation at 3343×g for 20 min into a high density fraction that was collected as a pellet and a low density supernatant fraction. Again, the high follistatin fraction was found to be the high density fraction. The analysis of the follistatin content is shown below:

| Fraction | Follistatin [µg/kg] |
| --- | --- |
| Protein, before centrifugation | 15 |
| Egg white, pellet | 33 |
| Whole egg, before centrifugation | 23 |
| Whole egg, pellet | 41 |
| Egg yolk, before centrifugation | 4 |
| Egg yolk, pellet | 36 |

These results show that the separation of egg yolk, whole egg or egg white into a higher density fraction, corresponding to egg yolk membranes and chalazae, results in an increased concentration of follistatin, wherein this fraction after the preservation step, preferably with subsequent drying, yields a composition having an increased concentration of follistatin.

Preferably, the egg yolk, whole egg or egg white was not homogenized prior to the separation, e.g. the egg yolk, whole egg or egg white was allowed to pass through a wide sieve or has was only stirred to break the egg yolk membranes to allow the egg yolk to leak out, preferably without breaking the egg yolk membranes or chalazae into small pieces.

The egg yolk powder was mixed at room temperature in batches with hardened plant-based fat, melting temperature 65-70° C., at 50 wt.-% each to form a powder mixture. This premix was metered into the inlet end of a twin screw extruder (Type 44, Buhler). The extruder barrel was temperature-controlled to 70° C. in a first section adjacent to the inlet end, to 30° C. in an adjacent second section, and to 5° C. in a third section adjacent to the die. In the process, the temperature control medium (1:1 glycol:water) in the first and second sections flowed in co-current with the conveying direction of the extruder, and in the third section flowed in counter-current. The metered premix liquefied in the first section during rotation of the screws (approx. 100 rpm). The extrudate strands discharging from the die plate had a temperature of approx. 30° C. were cut into pellets by rotating knives. It is assumed that the rotation of the screws and the resulting pressure of 14.7 bar measured in the extruder were sufficient to keep the mixture sufficiently malleable or flowable to be conveyed through the die even at a temperature of the mixture of below the melting temperature of the fat.

Alternatively, the egg yolk powder was mixed at 60 wt.-% with 40 wt.-% of the fat (melting point 65-70° C.) to form a powdery premix. The first section of the extruder adjacent to the inlet port was temperature-controlled to 60° C., the adjacent downstream second section was temperature-controlled to 25° C., and the adjacent third section, to which the extruder die plate is connected, was temperature-controlled to 0° C. In the first and second sections, the temperature control medium flowed in co-current flow with the conveying direction of the extruder, and in the third section flowed in counter-current flow. Optionally, between the first section and the inlet end, an additional extruder section was arranged which was not temperature-controlled. This additional extruder section does not appear to have any significant effect. Immediately after discharge from the die plate, a temperature of 24.3° C. was measured for the extrudate strands from the mixture, approx. 40 to 45 K below the melting temperature of the fat. The pressure in the extruder was approx. 16 to 17 bar.

Further alternatively, the first section of the extruder barrel adjacent to the inlet end was not temperature-controlled by temperature control medium, the adjacent second section was temperature-controlled to 70° C., the adjacent third section was temperature-controlled to 30° C., an adjacent fourth section adjacent to which the die plate was connected was temperature-controlled to 5° C. Therein, the temperature control medium flowed in counter-current to the conveying direction of the extruder. A powdered premix of egg yolk powder and powdered plant-based fat (melting temperature 65-70° C.), each 50 wt.-%, was again produced and metered into the inlet end of the extruder. A pressure of 14.7 bar was measured in the extruder, at the extruder outlet the mixture had a temperature of at maximum 40 K or of at maximum 30 K, e.g. approx. 35 to 40 K, below the melting temperature of the fat.

The respective pellet-shaped product of dry egg yolk encapsulated in the fat was stable against moisture and pourable.

Example 2: Production of a Liquid Ingredient Encapsulated by Fat

Liquid egg yolk, preserved or resp. sterilized according to a process of example 1, was used as an example of a liquid ingredient, plant-based fat (melting temperature 65-70° C.) was used as fat. The twin-screw extruder (Type 44, Buhler) was temperature-controlled to 60° C. in a first section adjacent to the inlet end, to 10° C. in the downstream adjacent second section, and to 0° C. in the third section downstream adjacent thereto. In the first and second sections, the temperature control medium flowed in the same direction as the conveying direction of the extruder, in the third section, the temperature control medium flowed in counter-current to the conveying direction of the extruder. Between the inlet end and the first section of the extruder, an optional non-temperature-controlled extruder section was arranged. The fat was metered into the inlet end at room temperature as a solid, powdery or lumpy, at 30 kg/h. The liquid egg yolk by an eccentric screw pump was continuously metered through a connecting port into the second section of the extruder at 10.5 kg/h. The screws were driven at 100 rpm.

The mixture discharging from the die plate as an extrudate strand was visually homogeneous and had a temperature of approx. 19-20° C. and thereby of approx. 45 to 50 K below the melting temperature of the fat. A pressure of approx. 11 bar was measured in the extruder. Preferably, the pellets produced by cutting the extrudate strand were subsequently dried, e.g. at room temperature to 4° C., until the pellets were superficially dry.

This example shows that the process is suitable for the production of fat-encapsulated liquid egg yolk, egg white or whole egg, alternatively animal blood serum.

Preferably, the pellets were filled into airtight plastic bags as packaging and were treated by temperature-controlling for 3 to 7 d (days) to 50 to 60° C., especially to 58° C. Therein, the fat had a higher melting temperature, e.g. of approx. 65-70° C.

For extrusion, e.g. an extruder was employed which was temperature-controlled to different temperatures in 4 zones as shown in FIG. 1. The extruder barrel was composed of 8 segments, and the screw extended along the entire length of the barrel. At the inlet end (zone I), the hydrogenated canola oil (HMF) was metered as powder into the extruder at 25 to 40 kg/h, e.g. 35 kg/h, the second section (zone II) was temperature-controlled to above the melting temperature of the hydrogenated canola oil, the low-melting fat (LMF) was temperature-controlled to 40 to 45° C. and was metered in liquid form into the second section by a metering pump (2.3 to 6.8 kg/h), the third section (zone III) and the fourth section (zone IV) were temperature-controlled to 0° C. in order to cool the mass to a temperature of approx. 17 to 28° C., measured immediately at the extruder outlet, and to immediately subsequently press the mass through a die plate having openings of 2 mm diameter, alternatively 0.5 or 1 mm diameter, and to cut the discharging solid strands with a rotating knife. The follistatin, powdered or liquid, or alternatively beetroot powder (RBP) as a model substance, was metered into the inlet end with the hydrogenated canola oil, or separately into the first section.

The screw was driven to 100 rpm, and the rotating knife had 6 blades rotating at 1200 rpm.

The mixture discharged from the die plate was solid, could be cut into dimensionally stable pellets, and required no further cooling, but was dimensionally stable at room temperature.

As a representative for follistatin, beetroot powder was used as an ingredient of the pellets to test the release from pellets. Prior to starting the in vitro digestion, 14 g of pellets were rinsed with distilled water for 2 min to rinse off beetroot powder present on the surface and thus to be able to determine the encapsulation efficiency in terms of release of beetroot powder from pellets by photometric determination. The in vitro test was carried out following Brodkorb et al, Nature Protocols 2019. The in vitro test initially includes a 3 minute oral phase in which the previously rinsed 14 g pellets are incubated with 14 mL of synthetic saliva at pH 7 (SSF) in the reactor of the semi-dynamic titration device at 37° C. For the initiation of the gastric phase, 17 mL of synthetic gastric juice having pH 3, as well as pepsin dissolved in 3 mL of SGF having pH 4.5, are added to the oral mixture and are incubated for 2 h at 37° C. Following the end of the gastric phase, 20 mL of the gastric mixture (half of the particles and half of the liquid) are mixed with 17 mL of synthetic intestinal fluid (SDF) having pH 7, as well as with pancreatin dissolved in 3 mL of SDF, and bile salts (CAS No. 8008-63-7, product No. SC-214601, available from Santa Cruz Biotechnology, Heidelberg) and are incubated for 2 h at 37° C. The pH value during semi-dynamic digestion is computer-set by the addition of acid and base in the oral phase to pH 7, in the gastric phase to pH 3.2 for 10 min, to pH 2.8 for 20 min, to pH 1.8 for 40 min, to pH 1.7 for 60 min, and to pH 1.5 for 120 min, and during the intestinal phase to pH 6.5 for 120 min. Switching between the individual digestive phases is carried out manually.

The release of the ingredient, represented by the beetroot powder, was determined in in vitro tests following surface washing of pellets to remove loose powder. The release was determined photometrically in the free solution.

Figure 2:
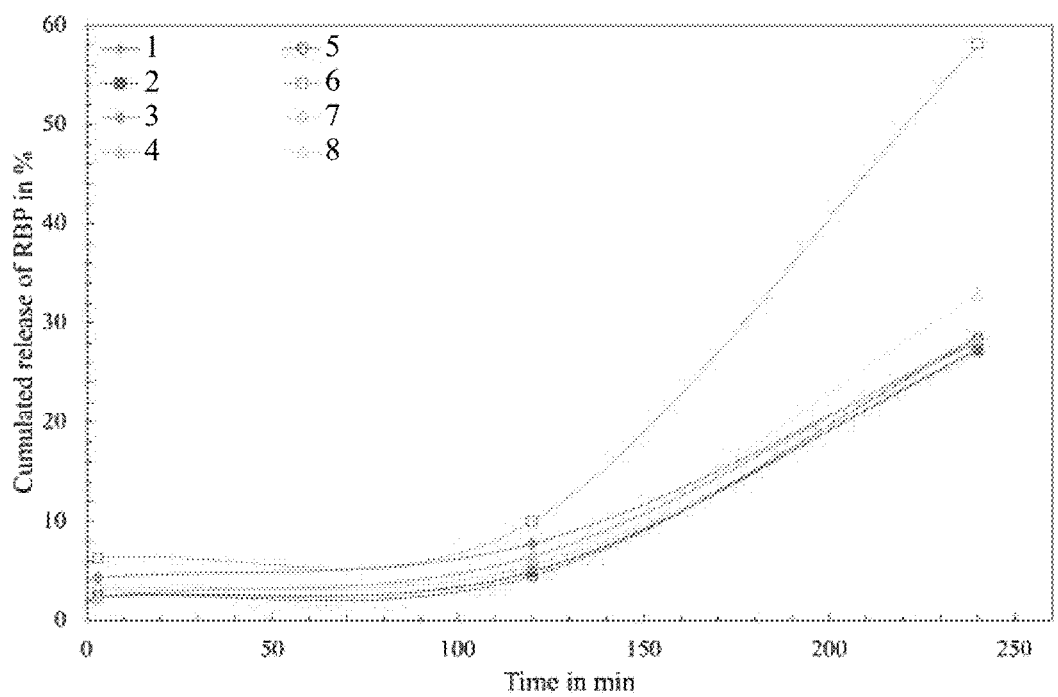
FIG. 2 shows the release of the model ingredient beetroot for 12% canola oil (1), 12% palm kernel fat.
Figure 3:
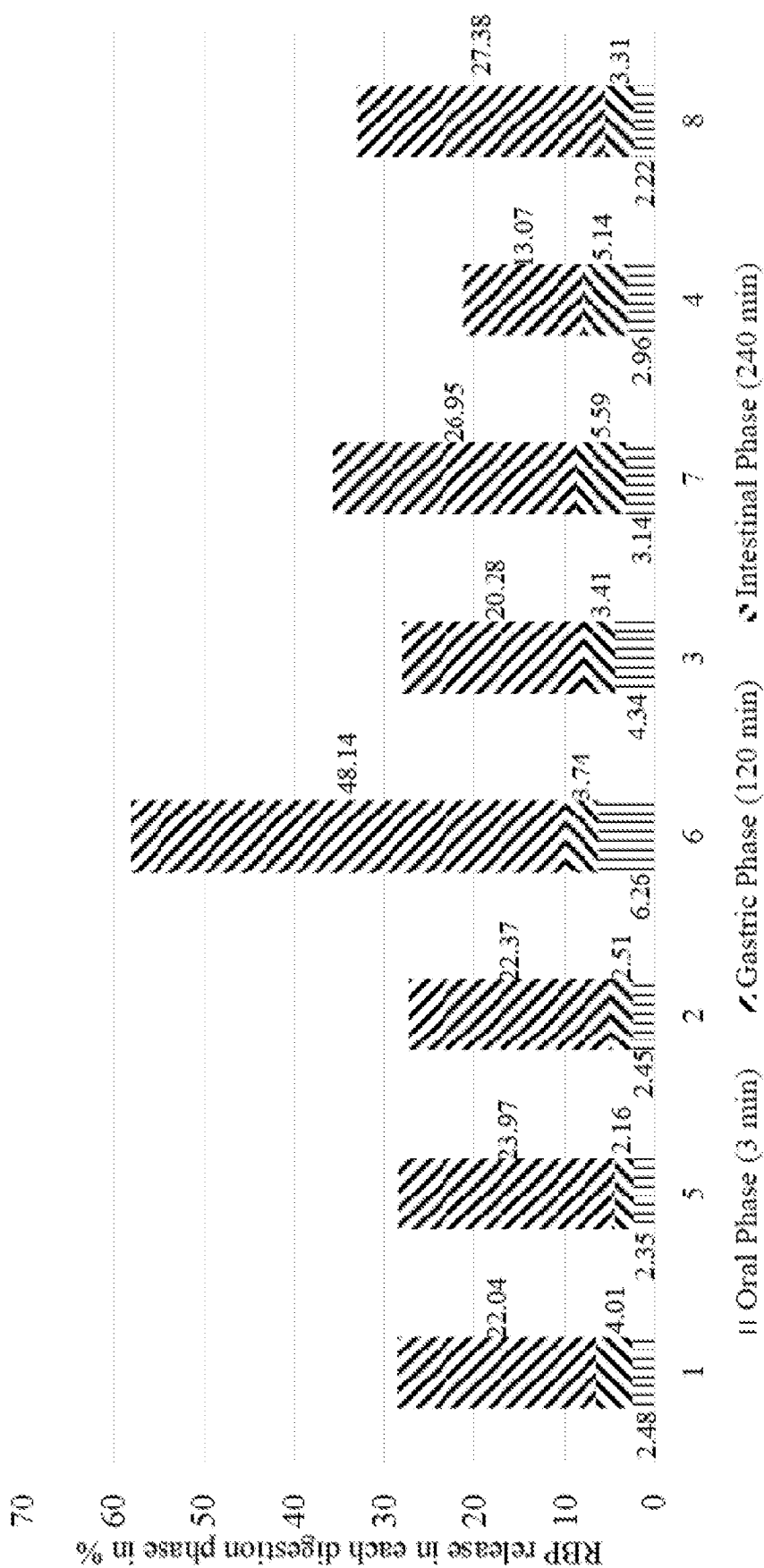
FIG. 3 shows the total release following the in vitro digestion.

FIG. 2 shows the release of the model ingredient beetroot for 12% canola oil (1), 12% palm kernel fat (2), 12% coconut fat having a melting point 22-26° C. (3), 12% coconut fat having a melting point 23-26° C. (4), 16% canola oil (5), 16% palm kernel fat (6), 16% coconut fat having a melting point 22-26° C. (7), 16% coconut fat having a melting point 24-26° C. (8) is shown in FIG. 2 over the time of the in vitro digestion, FIG. 3 shows the total release following the in vitro digestion.

This result shows that the pellets result in a delayed release of the majority of the ingredient of up to 48% in the intestinal phase (resorption site), while in the oral and gastric phases they show a low release or resp. are stable and protect the encapsulated component from acidic gastric juice.

The fat mixture including 16% low-melting palm kernel fat is particularly advantageous, as the proportion of released beetroot powder in the intestinal phase is almost twice as high in comparison to fat capsules with canola oil or one of the coconut fats. Also, the pellets having palm kernel fat have been found to have a good stability and good protection during the oral and gastric phases.

Overall, the results show that pellets produced according to the invention from ingredient encapsulated by fat, especially having a portion of low-melting fat, allow for a targeted release of the ingredient in the small intestine.

The invention claimed is:

1. A process for producing fat-encapsulated follistatin, the process comprising the steps of a) metering fat having a melting point of at least 40° C. into an extruder, b) heating the fat to a melting temperature of the fat in the extruder during rotation of a screw of the extruder, c) metering follistatin into an extruder barrel of the extruder to mix with the fat at the melting temperature of the fat and produce a flowable mixture of the follistatin and the fat, d) cooling the flowable mixture in a downstream adjacent section of the extruder barrel to a temperature of at least 10 K below the melting temperature of the fat to form a cooled mixture, e) subsequently discharging the cooled mixture through an extruder die, and f) comminuting the cooled mixture after discharge from the extruder die to produce pellets of fat-encapsulated follistatin.

2. The process according to claim 1, wherein the follistatin is provided within raw material from one or more of raw liquid egg yolk, whole egg or egg white originating from bird eggs, raw animal blood serum, or a fraction thereof, at or below 38° C.

3. The process according to claim 1, comprising providing the follistatin by a step of precipitating follistatin containing fraction from soluble protein of raw liquid egg yolk, whole egg or egg white derived from bird eggs, or raw animal blood serum, by precipitating a soluble protein fraction containing follistatin and separating the precipitated soluble protein fraction, and sterilizing or preserving one of the soluble protein fraction and the follistatin containing fraction.

4. The process according to claim 1, wherein the fat and the follistatin are metered into a same location of the extruder.

5. The process according to claim 1, wherein after the heating of the fat, which has a melting point of at least 50° C., to at least its melting temperature in the step b) and prior to the cooling of the step d), additionally a low-melting fat, which has a melting point of maximally 40° C., is metered into the extruder to maximally 20 wt.-% of a total of fats metered into the extruder.

6. The process according to claim 1, wherein in the step d) the cooling is carried out until the flowable mixture, after discharging from the extruder die, has a temperature which is in a range of 50 K to 10 K below the melting temperature of the fat.

7. The process according to claim 1, wherein the flowable mixture contains at least 5 wt.-% follistatin.

8. The process according to claim 1, wherein the fat is hydrogenated plant-based fat and/or hardened fish oil, or a mixture of the hydrogenated plant-based fat and/or the hardened fish oil, and the melting temperature of the fat is at least 40° C.

9. The process according to claim 1, wherein the follistatin is liquid prior to the step c).

10. The process according to claim 1, wherein the follistatin is dried prior to the step c).

11. The process according to claim 1, wherein the fat consists of hydrogenated plant-based fat.

12. The process according to claim 1, wherein the melting temperature of the fat is determined by differential scanning calorimetry.

13. The process according to claim 1, comprising a step of g) drying the pellets.

14. The process according to claim 1, comprising providing the follistatin for the metering of the step c) by treatment of raw material containing the follistatin by a high-pressure treatment of at least 4500 bar for at least 1 min, and/or by treatment of the raw material in a pulsed electric field of at least 5 kV/cm at a flow rate of 30 L/h.

15. The process according to claim 13, wherein subsequent to the step f) the pellets are treated by temperature-controlling the pellets to a temperature of at least 2 to 10 K below the melting temperature of the fat and at least 50° C. for at least 1 day.

16. The process according to claim 15, wherein the pellets are filled into airtight packages prior to the temperature-controlling.

* * * * *